(12) United States Patent
Schmidt et al.

(10) Patent No.: US 12,186,113 B2
(45) Date of Patent: Jan. 7, 2025

(54) METHOD FOR EVALUATING AN ANGIOGRAPHIC DUAL-ENERGY COMPUTED TOMOGRAPHY DATASET, EVALUATION FACILITY AND NON-TRANSITORY ELECTRONICALLY READABLE DATA CARRIER

(71) Applicant: Siemens Healthineers AG, Forchheim (DE)

(72) Inventors: Bernhard Schmidt, Fuerth (DE); Thomas Allmendinger, Forchheim (DE); Tristan Nowak, Erlangen (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 205 days.

(21) Appl. No.: 18/057,821

(22) Filed: Nov. 22, 2022

(65) Prior Publication Data

US 2023/0165542 A1 Jun. 1, 2023

(30) Foreign Application Priority Data

Nov. 29, 2021 (DE) ...................... 10 2021 213 438.6

(51) Int. Cl.
*A61B 6/03* (2006.01)
*A61B 6/00* (2006.01)
(Continued)

(52) U.S. Cl.
CPC ............ *A61B 6/032* (2013.01); *A61B 6/4241* (2013.01); *A61B 6/482* (2013.01); *A61B 6/582* (2013.01)

(58) Field of Classification Search
CPC ....... A61B 6/032; A61B 6/4241; A61B 6/482; A61B 6/582; A61B 6/48; A61B 6/505; A61B 6/481; A61B 6/504; A61B 6/5205; A61B 6/5217; A61B 6/503; A61B 6/52; A61B 6/54; A61B 6/583; G06T 7/0012; G06T 2207/10081; G06T 2207/30048; G06T 2207/30101
See application file for complete search history.

(56) References Cited

U.S. PATENT DOCUMENTS

2010/0328313 A1* 12/2010 Zamyatin ............. G06V 10/763
382/131
2017/0301082 A1 10/2017 Allmendinger et al.
(Continued)

FOREIGN PATENT DOCUMENTS

DE   102016221684 A1   6/2017
DE   102016207437 A1   11/2017
WO   WO 2019072554 A1   4/2019

OTHER PUBLICATIONS

Yamak et al., "Coronary calcium quantification using contrast-enhanced dual-energy computed tomography scans", Journal of Applied Clinical Medical Physics, vol. 14, No. 3, pp. 203-214. (Year: 2013).*

(Continued)

*Primary Examiner* — Kiho Kim
(74) *Attorney, Agent, or Firm* — Harness, Dickey & Pierce, P.L.C.

(57) ABSTRACT

One or more example embodiments provides a method for evaluating an angiographic dual-energy computed tomography dataset recorded using a contrast agent comprising iodine to determine a quantitative calcium score.

20 Claims, 3 Drawing Sheets

(51) Int. Cl.
    *A61B 6/42*           (2024.01)
    *A61B 6/58*           (2024.01)

(56) References Cited

U.S. PATENT DOCUMENTS

2017/0311917 A1   11/2017   Allmendinger et al.
2021/0407056 A1   12/2021   Prevrhal et al.

OTHER PUBLICATIONS

Song, Inyoung, et al. Virtual non-contrast CT using dual-energy spectral CT: feasibility of coronary artery calcium scoring. Korean journal of radiology, 2016, 17. Jg., Nr. 3, S. 321-329.
Sodickson, Aaron D., et al:Dual energy CT in clinical routine: how it works and how it adds value. Emergency Radiology, 2021, 28. Jg., Nr. 1, S. 103-117.
McCollough, Cynthia H. et al. "Coronary Artery Calcium: A Mult-institutional, Multimanufacturer International Standard for Quantification at Cardiac CT" Radiology, vol. 243, No. 2, pp. 527-538, May 2007 // DOI: 10.1148/radiol.2432050808.
Agostini, Andrea, et al. Dual-energy CT: theoretical principles and clinical applications. La radiologia medica, 2019, 124. Jg., Nr. 12, S. 1281-1295.

* cited by examiner

METHOD FOR EVALUATING AN ANGIOGRAPHIC DUAL-ENERGY COMPUTED TOMOGRAPHY DATASET, EVALUATION FACILITY AND NON-TRANSITORY ELECTRONICALLY READABLE DATA CARRIER

CROSS-REFERENCE TO RELATED APPLICATION(S)

The present application claims priority under 35 U.S.C. § 119 to German Patent Application No. 10 2021 213 438.6, filed Nov. 29, 2021, the entire contents of each of which are incorporated herein by reference.

FIELD

One or more example embodiments of the present invention relates to a method for evaluating an angiographic dual-energy computed tomography dataset recorded using a contrast agent comprising iodine. In addition, one or more example embodiments of the present invention relates to an evaluation facility, to a computer program and to an electronically readable data carrier.

STATE OF THE ART

Coronary heart disease is one of the most frequent causes of death. In order to clarify a potential risk which is caused by a possible coronary heart disease, it is usual in clinical routine to carry out a scan of the heart of the patient using computed tomography, said scan also indicating the coronary vessels (also referred to as coronary blood vessels). In this context, two variations are known, both of which are frequently used for the same patient.

On the one hand, it is known to carry out a dedicated scan without contrast agent, in order to be able to quantify the existing quantity of "hard" calcifications. Here the computed tomography dataset is evaluated in order to calculate a calcium score, for instance the known and common Agatston score. This is a unitless measure for quantifying the calcification of the coronary arteries, wherein for its determination for instance via an operator, calcifications to be taken into account in the coronary arteries can be selected and an observation of the thresholds for these is carried out. In other words, all pixels of the coronary arteries are counted for which the image value (attenuation value) exceeds at least one threshold value.

In addition to the calcium scoring, there is also the possibility of what is known as coronary computed tomography angiography (CCTA), wherein the heart and the region of the coronary vessels is examined with the aid of a high-dose contrast agent injection of a contrast agent typically comprising iodine in the arterial phase so that the coronary blood vessels can be examined with respect to possible lesions, in particular stenoses.

The problem here is that a standalone computed tomography scan has to be carried out in each case with a corresponding dose load for the generation of a calcium score and CCTA vascular diagnostics. Due to the contributions of high attenuation values as a result of the iodine contrast agent, counting in CCTA datasets is not possible.

It is essentially known to carry out CCTA scans in a spectrally-resolved manner, for instance using a photon-counting x-ray detector; that means to determine an angiographic dual-energy computed tomography dataset, in which a first and a second attenuation value, which are assigned to different energy spectra, are assigned to each pixel as image values. For angiographic dual-energy computed tomography datasets of this type, it has already been proposed in the prior art to carry out a base material decomposition into two materials, namely iodine and soft tissue, so that an iodine image dataset and a non-iodine image dataset are generated, wherein the latter is frequently referred to as "virtual non-contrast" image or VNC image. By subtracting the proportions of iodine, it could be assumed that a VNC image could be suited to the calcium scoring. This is not the case, however, since in terms of spectral properties the material calcium lies between iodine on the one hand and soft tissue on the other hand, so that one part of the calcium material (which also comprises bone material) is partly recorded in the iodine image, and the other part in the VNC image. As a result of this division of the proportion of calcium, the VNC image loses its quantitative properties in respect of the calcium scoring and for this reason cannot be used meaningfully.

SUMMARY

One or more example embodiments of the present invention enables determining a calcium score also from an angiographic computed tomography dataset recorded using iodine contrast agent.

In order to achieve this object, according to one or more example embodiments of the present invention, a method, an evaluation facility, a computer program and an electronically readable data carrier are provided in accordance with the independent claims. Advantageous embodiments will become apparent from the dependent claims.

According to one or more example embodiments, a method for evaluating an angiographic dual-energy computed tomography dataset recorded using a contrast agent comprising iodine, the angiographic dual-energy computed tomography dataset including an image vector for each pixel, the image vector being formed by a first attenuation value assigned to a high-energy spectrum and a second attenuation value assigned to a low-energy spectrum, the method comprises specifying a calcium base vector and an iodine base vector in a two-dimensional dual-energy space spanned by the first attenuation value as an x-axis and the second attenuation value as a y-axis, a base material decomposition being based on the two-dimensional dual-energy space; projecting all image vectors below a straight line in the dual-energy space onto the straight line to determine a modified dual-energy computed tomography dataset, the straight line being defined by the calcium base vector; performing the base material decomposition of the modified dual-energy computed tomography dataset to determine a calcium image dataset; and determining a quantitative calcium score from the calcium image dataset.

According to one or more example embodiments, the base material decomposition is restricted to a permissible attenuation value range in the dual-energy space, wherein the determining the calcium image dataset outside of the permissible attenuation value range includes determining mixed image attenuation values from the first attenuation value and the second attenuation value.

According to one or more example embodiments, the permissible attenuation value range includes non-negative attenuation values.

According to one or more example embodiments, the determining the quantitative calcium score includes selecting an amount of the calcium base vector for setting a calcium contrast based on calibration data.

According to one or more example embodiments, the selecting the amount of the calcium base vector includes recording calibration datasets with contrast agent for at least one calibration object, wherein a reference value of the quantitative calcium score is known for the calibration object or is determined, and selecting the amount to be set such that an evaluation value of at least one calibration dataset corresponds to the reference value.

According to one or more example embodiments, the method further includes selecting weightings of the first attenuation value and the second attenuation value are to determine a mixed image attenuation value as a function of the selected amount when a mixed image outside of a permissible attenuation value range is used.

According to one or more example embodiments, the determining the quantitative calcium score determines the quantitative calcium score based on a user-side selection of calcifications in a displayed calcium image dataset.

According to one or more example embodiments, at least one of the determining the quantitative calcium score includes determining an Agatston score is determined as the quantitative calcium score, or evaluating the dual-energy computed tomography dataset for lesions in a coronary vascular tree, the dual-energy computed tomography dataset being a coronary computed tomography angiography dataset.

According to one or more example embodiments, the method further includes recording the dual-energy computed tomography dataset using at least one of two different transmit spectra of at least one x-ray source or a photon-counting x-ray detector.

According to one or more example embodiments, an evaluation facility comprises a first interface configured to receive an angiographic dual-energy computed tomography dataset recorded using a contrast agent comprising iodine, the angiographic dual-energy computed tomography dataset comprises an image vector for each pixel, the image vector being formed by a first attenuation value assigned to a high-energy spectrum and a second attenuation value assigned to a low-energy spectrum; a storage means storing a calcium base vector and an iodine base vector in a two-dimensional dual-energy space spanned by the first attenuation value as an x-axis and the second attenuation value as a y-axis, a base material decomposition being based on the two-dimensional dual-energy space; a modification unit configured to determine a modified dual-energy computed tomography dataset by projecting all image vectors in the dual-energy space below a straight line onto the straight line, the straight line defined by the calcium base vector; a base material decomposition unit configured to perform the base material decomposition of the modified dual-energy computed tomography dataset to determine a calcium image dataset; a determination unit configured to determine a quantitative calcium score from the calcium image dataset; and a second interface configured to output the quantitative calcium score.

According to one or more example embodiments, a non-transitory computer readable medium includes instructions that, when executed by an evaluation facility, cause the evaluation facility to perform a method according to one or more example embodiments.

According to one or more example embodiments, a non-transitory electronically readable data carrier includes instructions that, when executed by an evaluation facility, cause the evaluation facility to perform a method according to one or more example embodiments.

BRIEF DESCRIPTION OF THE DRAWINGS

Advantages and details are disclosed in the exemplary embodiments described below and by reference to the drawing, in which.

DETAILED DESCRIPTION

Figure 1:
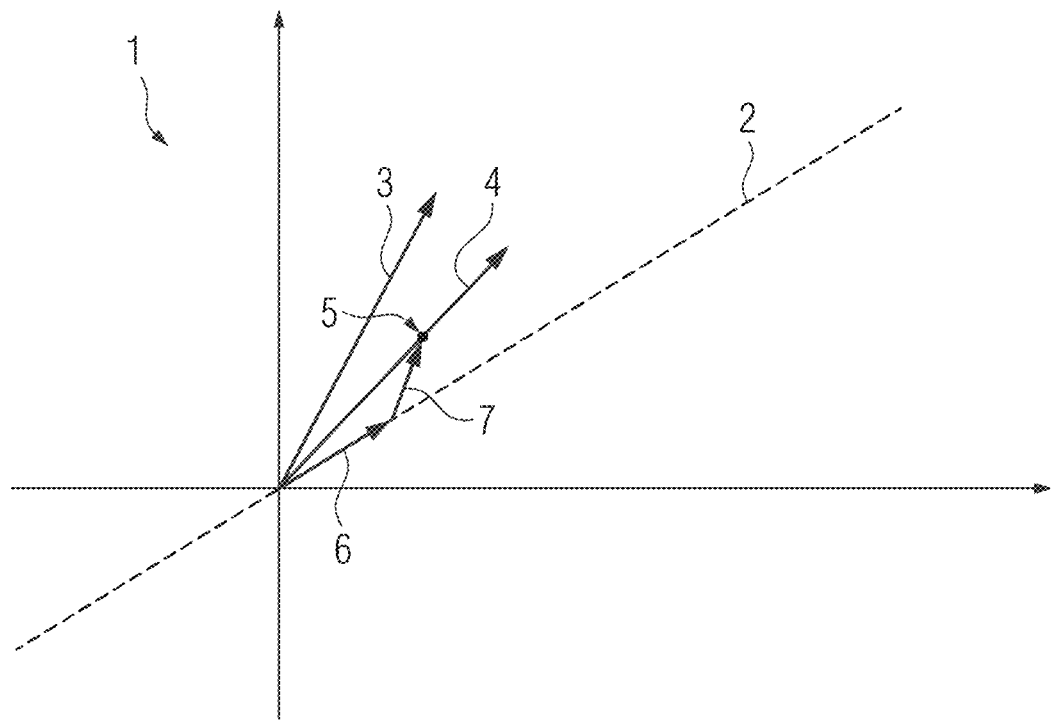
FIG. 1 shows a diagram to explain the problem underlying one or more example embodiments of the present invention.

With a method of the type cited in the introduction, the following steps are provided in accordance with one or more example embodiments of the present invention in order to determine a quantitative calcium score:

specifying a calcium base vector and an iodine base vector in the two-dimensional dual-energy space spanned by the first attenuation value as an x-axis and the second attenuation value as a y-axis as the basis of a base material decomposition, projecting all image vectors, which lie in the dual-energy space below a straight line defined by the calcium base vector, onto the straight line in order to determine a modified dual-energy computed tomography dataset, carrying out the base material decomposition of the modified dual-energy computed tomography dataset in order to determine a calcium image dataset, and determining the quantitative calcium score from the calcium image dataset.

Spectrally-resolved computed tomography data is therefore used which comprises attenuation values for two energy spectra, namely a high-energy spectrum and a low-energy spectrum, wherein the high-energy spectrum has a higher energy mean value than the low-energy spectrum. The energy spectra are frequently referred to here by equivalent or used tube voltage values of an x-ray radiation source, wherein an equivalent designation relates to the appearance corresponding to the x-ray image recorded with the tube voltage. In the prior art, combinations of an 80 kV low-energy spectrum with a 140 kV high-energy spectrum or a 90 kV low-energy spectrum with a 150 kV high-energy spectrum are frequently used; x-ray images which are not spectrally resolved relate in most cases to a 120 kV spectrum, to which an effective energy mean value of 70 keV corresponds.

The inventively provided generation of a suitably calculated non-iodine image, which can also be referred to as a "virtual non-iodine" image or VNI image, in other words of the calcium image dataset, is based on a modified base material decomposition into two materials with additional auxiliary conditions. The two-material system used consists of the base materials iodine and calcium. Since non-physical decompositions may however result for image vectors lying outside of the region lying between the base vectors, it is proposed to perform a projection on precisely this straight line, at least within a permissible attenuation value range, which can be defined for positive HU values for instance, for the image vectors originating in particular from the soft tissue and suchlike, and lie below the calcium base vector or the straight line defined by this, so that a non-physical material decomposition is avoided. Typically only image vectors caused by noise lie above the iodine base vector; on the other hand the developing iodine image dataset is not relevant to the evaluation discussed here.

In respect of the permissible attenuation value range, it is therefore also expedient within the scope of the present invention if the base material decomposition is limited to a permissible attenuation value range in the dual-energy space, wherein in order to determine the calcium image dataset outside of the permissible attenuation value range, mixed image attenuation values are determined from the first and the second attenuation value, in particular as a mixed image assigned to a reference tube voltage. Here, as already mentioned, the permissible attenuation value range can expediently be selected comprising non-negative attenuation values, in particular HU values. Procedures of this type are basically known in the prior art, wherein for instance for a 120 kV-equivalent mixed image comprising 90 kV and 150 kV attenuation values it is possible to determine that the 90 kV attenuation values (second attenuation values) shrink to 60%, the 150 kV attenuation values (first attenuation values) to 40%.

It would now essentially be conceivable to further limit the permissible attenuation range, for instance to all image vectors lying between the iodine base vector and the calcium base vector; however this can result in unwanted image artifacts in the calcium image dataset on account of non-physical material decompositions, for instance due to thresholding effects. In particular, if an operator is to select calcifications to be used to determine the calcium score, the occurrence of such variations in the known images reduces the operator's confidence and also the manual evaluability, wherein with an automated approach the latter could also result in problems. One or more example embodiments of the present invention therefore particularly advantageously proposes a projection of the corresponding image vectors onto the calcium base vector, since it has been shown here that a calcium image leaving behind a typical image impression is produced, which results in a robust and reliable evaluability with respect to the calcium score.

The present invention therefore enables a calcium image dataset to be derived, in a particularly reliable and robust manner, from an angiographic dual-energy computed tomography dataset, for instance a spectrally-resolved CCTA dataset, which is suited to the quantitative calcium scoring. In this way, a separate, native scan can be saved for the calcium scoring, which reduces the overall dose load for the patient via the computed tomography examination, and also reduces the required examination time. In other words, both angiographic evaluation results, for instance with respect to stenoses, and also a calcium scoring can be achieved with considerably less effort.

It should be noted here that while it is essentially conceivable to generate the dual-energy computed tomography dataset using two different transmit spectra of at least one x-ray radiation source, it is clearly preferred according to the present invention to record these using a photon-counting x-ray detector. This not only enables spectrally-resolved computed tomography data to be determined in a single measurement process, but also has intrinsic advantages for the consistency of the data. During photon-counting, a single photon detector can be used, for instance, to convert the incident photon into an electrical signal using a scintillator and/or a converter, the strength of said electrical signal depending on the photon energy.

After determining the modified dual-energy computed tomography dataset in the permissible attenuation value range of the dual-energy space, the base material decomposition can be carried out, as essentially known. Different base material decomposition algorithms, such as those already proposed in the prior art, can finally be used. Here the base material decomposition can take place in the projection space; however an application in the image space, in other words after the reconstruction, is preferred. HU values (Hounsfield Units) are then present as attenuation values.

In a particularly advantageous development of the present invention, provision can be made for the amount of the calcium base vector for setting a calcium contrast in order to determine the quantitative calcium score to be selected as a function of calibration data. In other words, there is the possibility, as an additional intervention into the base material decomposition or its fundamentals, to define the length of the calcium base vector so as to differ from a standard length, for instance 1, which results in a scaling of the attenuation values in the calcium image dataset. This degree of freedom in the scaling can be used to set the calcium contrast, namely so that a quantitatively exact calcium score can be determined.

Specifically, it can be provided here, in order to determine an amount to be set for the calcium base vector:

for at least one calibration object, in particular a phantom, to record at least one calibration dataset with contrast agent, wherein a reference value of the quantitative calcium score is known for the calibration object or is determined, and by evaluating the at least one calibration dataset using different test amounts of the calcium base vector, for an amount to be set to be determined so that the evaluation value determined in the evaluation for the quantitative calcium score corresponds as accurately as possible to the reference value.

Here an optimization method can in particular be used.

In other words, it is possible to set the amount of the calcium base vector with the aid of suitable calibration data so that the calcium score can be calculated quantitatively particularly accurately from the calcium image dataset, even if unusual attenuation values possibly occur there. While it is essentially conceivable to use any phantoms and/or also clinical data, wherein the calcium score can be determined from a calibration dataset recorded without contrast agent, a particularly advantageous embodiment of the present invention provides for a phantom to be used for which the exact value of the calcium score is already known. A phantom of this type was proposed in another context in an article by C. H. McCollough et al., "Coronary artery calcium: a multi-institutional, multimanufacturer international standard for quantification at cardiac CT", Radiology 243 (2007), pages 527-538, for instance. In this case, it is only necessary to record at least one calibration dataset with contrast agent, which is spectrally resolved, and in an optimizing manner to set the amount of the calcium base vector so that the evaluation value of the calcium score corresponds as exactly as possible to the previously known reference value.

As already mentioned, the scaling of the calcium base vector can result in the attenuation values obtained in the calcium image dataset, in particular HU values, not corresponding to the attenuation values expected for instance for a native calcium scoring computed tomography dataset, in particular in respect of the calcium itself. For this purpose, an extremely accurate quantitative determination of the calcium score is enabled, however. In other words, it can also be said that with respect to the quantitative aspects, everything is subordinate to determining the calcium score.

In this context, in a preferred embodiment, provision can also be made for the weightings of the first and the second attenuation value for determining the mixed image attenuation value to be selected as a function of the set amount when a mixed image outside of the permissible attenuation value range is used. If the set amount of the calcium base vector leads for instance to the permissible attenuation value ranges treated accordingly by the base material decomposition acting more like a 140 kV x-ray image, in order to achieve a uniform overall impression of the calcium image dataset, it may be expedient also to adjust the reference tube voltage accordingly for the mixed image, for instance if the calcium image dataset is to be output to an operator in order to mark calcifications to be taken into account.

In a specific embodiment of the present invention, provision can generally also be made for the calcium score to be determined on the basis of a user-side selection of calcifications in the displayed calcium image dataset. The calcium image dataset can thus be output to an operator, who, as essentially known, marks any calcifications which are relevant to the calcium score, in the case of the coronary vessels, calcifications located in the coronary vessels for instance. On this basis, the calcium score can then be determined, whereby it should be noted that it is naturally generally also conceivable to determine a number of calcium scores and/or to determine the calcium score in a spatially-resolved or region-resolved manner.

In particular, the Agatston score can be determined here as a quantitative calcium score. The Agatston score is a unitless measure for quantifying calcifications, in particular of the coronary arteries, wherein in this regard different threshold values can be used, for instance. It is conceivable for instance to count a pixel exceeding a threshold value of 130 HU once, a pixel exceeding a threshold value of 200 HU twice and a pixel exceeding a threshold value of 300 HU four times.

The present invention can be applied particularly advantageously, as already indicated, to coronary examinations. Provision can thus be made for the dual-energy computed tomography dataset to be a coronary computed tomography angiography dataset (CCTA), which is further subjected to an evaluation in order to detect lesions in the coronary vascular tree, in particular stenoses.

In addition to the method, the present invention also relates to an evaluation facility, in particular as part of an x-ray facility and/or an evaluation workstation computer, which evaluation facility has:
- a first interface for receiving an angiographic dual-energy computed tomography dataset recorded using a contrast agent comprising iodine, which dual-energy computed tomography dataset comprises an image vector for each pixel, said image vector being formed by a first attenuation value assigned to a high-energy spectrum and a second attenuation value assigned to a low-energy spectrum,
- a storage means, in which a calcium base vector and an iodine base vector are stored in the two-dimensional dual-energy space spanned by the first attenuation value as an x-axis and the second attenuation value as a y-axis as the basis of a base material decomposition,
- a modification unit for determining a modified dual-energy computed tomography dataset by projecting all image vectors, which lie in the dual-energy space below a straight line defined by the calcium base vector, onto the straight line,
- a base material decomposition unit for carrying out the base material decomposition of the modified dual-energy computed tomography dataset in order to determine a calcium image dataset,
- a determination unit for determining a quantitative calcium score from the calcium image dataset, and
- a second interface for outputting the quantitative calcium score.

In other words, the evaluation facility is embodied to carry out the inventive method. All descriptions regarding the method according to one or more example embodiments of the present invention apply similarly to the evaluation facility according to one or more example embodiments of the present invention, so that the advantages already cited can also be achieved therewith.

In order to realize the respective functional units, the evaluation facility can have at least one processor. The storage means can naturally also be used to store other data accumulated in the procedure. Developments of the method can be implemented by way of corresponding further functional units/subunits. In respect of setting the amount of the calcium base vector, the corresponding value can be stored in the storage means itself following its determination, but a corresponding setting unit can also be provided. It should be noted that if different combinations of high-energy spectra and low-energy spectra can occur, different underlying parameters with respect to the base material decomposition can naturally also be stored in the storage means, in particular base vectors assigned to different combinations, preferably including amounts set and to be determined in a calibration.

The evaluation facility can be part of an x-ray facility, in particular a computed tomography facility, in order therefore also to be able to provide the calcium score directly. The integration into a diagnostic system or specifically an evaluation workstation computer is also advantageous.

A computer program according to one or more example embodiments of the present invention can be loaded directly into the memory of an evaluation facility and has program means to perform the steps of a method according to one or more example embodiments of the present invention when the computer program is executed on the evaluation facility. The computer program can be stored on an electronically readable data carrier according to one or more example embodiments of the present invention which therefore comprises control information, which comprises at least one inventive computer program and is configured such that when the data carrier is used in an evaluation facility, an inventive method is carried out. The data carrier can be a non-transient data carrier, for example, a CD-ROM.

The following exemplary embodiments are explained in more detail using the example of a CCTA recording as an angiographic dual-energy computed tomography dataset. With a CCTA recording, a contrast agent containing iodine is administered in order to make vessels as clearly visible as possible. In this context, it is known to carry out a base material decomposition into soft tissue as a first material and iodine as a second material, so that an iodine image dataset and a soft tissue image dataset (frequently referred to as VNC image) are obtained. With examinations of the coronary vessels (coronary blood vessels), it is frequently desirable however also to obtain a calcium score, in particular what is known as the Agatston score. FIG. 1 explains why this is not possible on the basis of the VNC image.

The dual-energy space 1, which is spanned by the first attenuation value according to the high-energy spectrum on the x-axis and the second attenuation value according to the low-energy spectrum on the y-axis, is shown. A straight line 2 which indicates the direction of the soft tissue base vector is shown (for reasons of clarity, the soft tissue base vector itself is not shown). In addition to the soft energy base vector, an iodine base vector 3 is used for the base material decomposition. As the calcium base vector 4 indicates, image vectors, formed from the first and second attenuation value, for calcium values lie between iodine and soft tissue, so that for instance for the point 5 assigned to an image vector during the base material decomposition, a proportion 6 of this image vector is contained in the VNC image, another proportion 7 however in the iodine image dataset so that the VNC image is not suited to the quantitative calcium evaluation.

Figure 2:
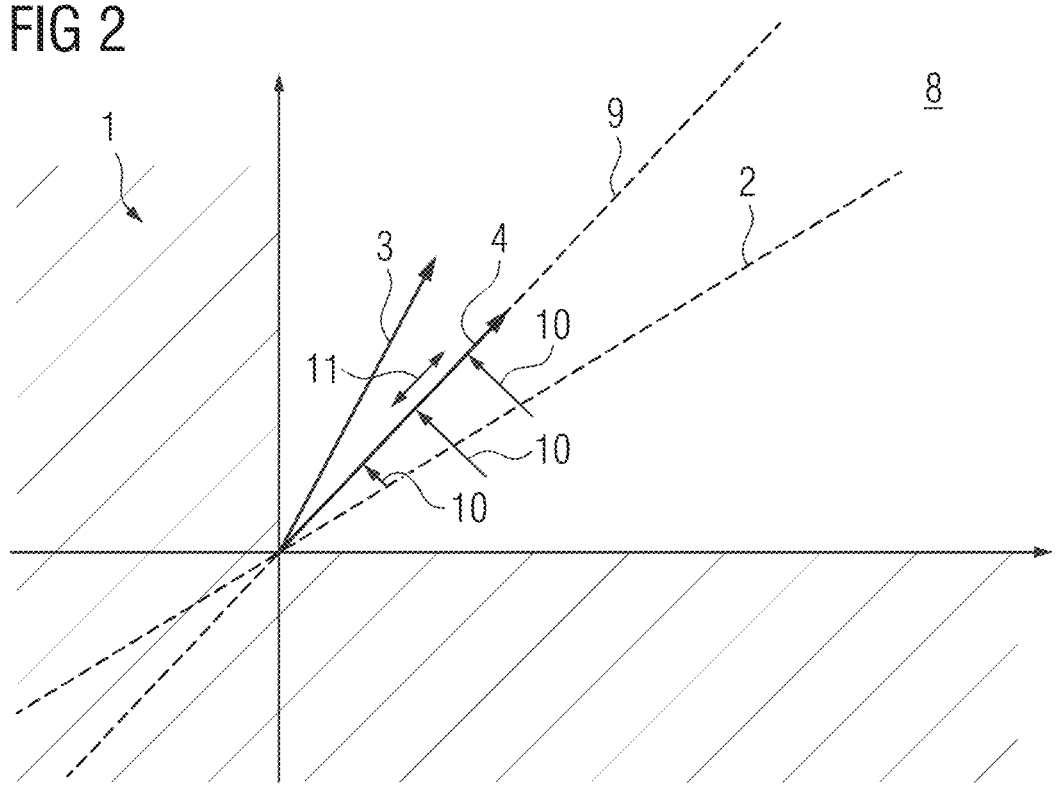
FIG. 2 shows a diagram to explain the approach according to one or more example embodiments of the present invention.

FIG. 2 explains how, conversely, in the scope of the present invention, the quantitative evaluation, here the determination of a quantitative calcium score, of an accessible calcium dataset is determined. A base material decomposition carried out with the iodine base vector 3 and the calcium base vector 4 forms the basis. Two measures are implemented in order to avoid non-physical results, however. On the one hand, all regions shown here hatched, which have negative HU values as attenuation values, are excluded so that the base material decomposition is restricted to a permissible range 8. Furthermore, a projection of all image vectors, which lie below the straight line 9 defined by the calcium base vector 4, is performed on this straight line, as indicated by the arrows 10. In order to ensure that as accurate a determination of the calcium score as possible takes place, the amount (in other words the length) of the calcium base vector 4 is adjusted as a further degree of freedom, as indicated by the arrow 11.

Figure 3:
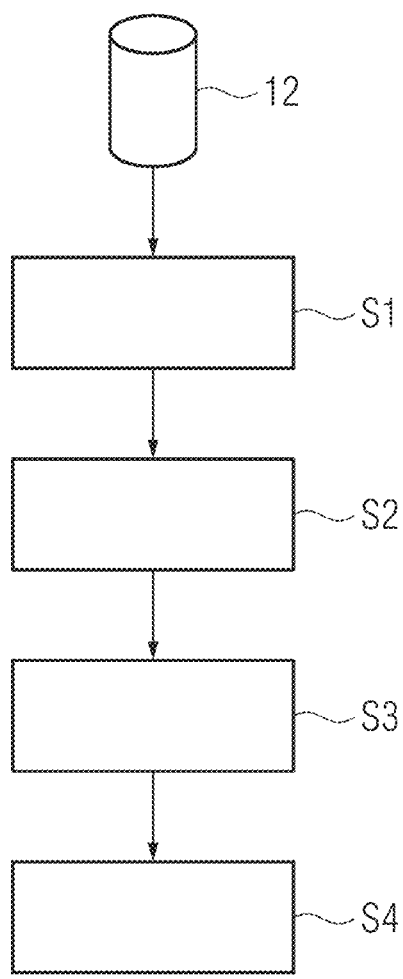
FIG. 3 shows a flow diagram of an exemplary embodiment of the method according to the invention.

This is all explained in more detail on the basis of the flow chart, shown in FIG. 3, of an exemplary embodiment of the inventive method.

Here, as already described, the starting point is the angiographic dual-energy computed tomography data set 12, in the present example a CCTA dataset. This was recorded in an energy-resolved manner using a photon-counting x-ray detector, wherein it would essentially also be conceivable to provide the spectral resolution by using different transmit spectra.

In a preparatory step 1, the dual-energy computed tomography dataset 12 is restricted to the permissible range 8; this means that all negative attenuation values, here HU values, are excluded from the base material decomposition via threshold treatment. In the hatched, excluded regions of negative attenuation values, the pixels of the calcium image dataset to be determined are filled with mixed image attenuation values, wherein the corresponding weighting, with which the first and the second attenuation value are taken into consideration, result at least partially as a function of the set amount of the calcium base vector 4, in order to obtain a uniform image impression in the end result.

For the permissible region 8, in step S2, a modification of all attenuation values then takes place in image vectors which lie below the straight line 9. To this end, the image vectors, as indicated by the arrows 10 in FIG. 2, are projected at a right angle onto the straight line 9. The image vector developed accordingly and lying on the straight line 9 is then used accordingly on the respective pixel in the modified dual-energy computed tomography dataset.

Then in step S3, the base material decomposition, as is essentially known in the prior art, is then carried out using the base vectors 3 and 4, wherein the amount of the calcium base vector 4 is adjusted, as described, so that the calcium contrast permits as exact a quantitative determination of the calcium score as possible. The result of step S3 is a calcium image dataset, which also contains the mixed image proportions already determined in step S2 in the hatched, impermissible regions.

In step S4, the quantitative calcium score, here the Agatston score, is determined in a known manner from the calcium image dataset, for instance on a threshold value basis. To this end, the calcium image dataset can be output in advance and calcifications, which are to be taken into consideration in the determination of the quantitative calcium score, can be marked by a user, for instance.

In order to set the amount of the calcium base vector 4, cf. arrow 11 in FIG. 2, a calibration takes place via a phantom for which a reference value of the Agatston score is already known. At least one calibration dataset is recorded from this in the same manner as subsequent angiographic dual-energy computed tomography datasets 12, wherein in an optimization method the amount of the calcium base vector 4 is determined, for which according to the evaluation described here, an evaluation value of the Agatston score is determined, which most accurately matches the reference value. The corresponding amount is then the amount to be set and can be stored in a storage means of the evaluation facility, which carries out the method.

Figure 4:
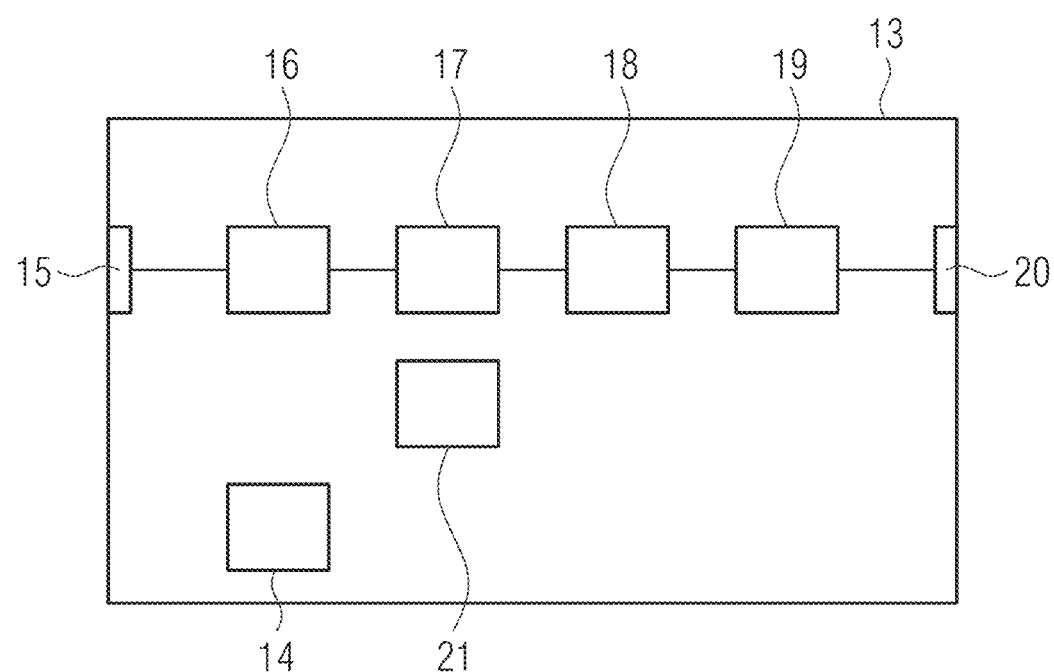
FIG. 4 shows the functional structure of an evaluation facility according to one or more example embodiments of the present invention.

A functional schematic diagram of an inventive evaluation facility 13 is shown in FIG. 4. Accordingly, the evaluation facility 13 firstly has a storage means 14, in which inter alia the base vectors 3, 4, including, in the case of the calcium base vector 4, the amount to be set, can be stored. The presence of a setting unit (not shown in more detail here) which carries out the calibration method described here is also conceivable for the amount of the calcium base vector 4. Here multiple sets of such base vectors 3, 4 can be provided in particular for different combinations of high-energy spectra and low-energy spectra of the x-ray radiation, of which the suitable one is then selected.

The angiographic dual-energy computed tomography dataset 12 to be evaluated can be received by way of a first interface 15. In a preparation unit 16, the permissible region 8 is selected and the impermissible regions of the calcium image dataset are filled with the mixed image, as described with respect to step S1 in FIG. 3. In a modification unit 17, the projection is then carried out according to step S2. The base material decomposition according to step S3 is then carried out in a base material decomposition unit 18, downstream of which is then arranged a determination unit 19 for determining the calcium score that can be output by way of a second interface 20.

It should be noted that the evaluation facility 13 can also have an evaluation unit 21, in which for instance further evaluations of the angiographic dual-energy computed tomography dataset 12 can take place, for instance a typical CCTA evaluation in order to define stenoses and suchlike. Its results can be output accordingly on the second interface 20.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module', 'interface' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing system or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium, storage means or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the invention has been illustrated and described in detail by way of exemplary embodiments, the invention is not restricted by the examples disclosed and other variations can be derived therefrom by a person skilled in the art without departing from the protective scope of the invention.

The invention claimed is:

1. A method for evaluating an angiographic dual-energy computed tomography dataset recorded using a contrast agent comprising iodine, the angiographic dual-energy computed tomography dataset including an image vector for each pixel, the image vector being formed by a first attenuation value assigned to a high-energy spectrum and a second attenuation value assigned to a low-energy spectrum, the method comprising:
    specifying a calcium base vector and an iodine base vector in a two-dimensional dual-energy space spanned by the first attenuation value as an x-axis and the second attenuation value as a y-axis, a base material decomposition being based on the two-dimensional dual-energy space;
    projecting all image vectors below a straight line in the dual-energy space onto the straight line to determine a modified dual-energy computed tomography dataset, the straight line being defined by the calcium base vector;
    performing the base material decomposition of the modified dual-energy computed tomography dataset to determine a calcium image dataset; and
    determining a quantitative calcium score from the calcium image dataset.

2. The method of claim 1, wherein the base material decomposition is restricted to a permissible attenuation value range in the dual-energy space, wherein the determining the calcium image dataset outside of the permissible attenuation value range includes,
    determining mixed image attenuation values from the first attenuation value and the second attenuation value.

3. The method of claim 2, wherein the permissible attenuation value range includes non-negative attenuation values.

4. The method of claim 3, wherein the determining the quantitative calcium score includes,
    selecting an amount of the calcium base vector for setting a calcium contrast based on calibration data.

5. The method of claim 4, wherein the selecting the amount of the calcium base vector includes,
    recording calibration datasets with contrast agent for at least one calibration object, wherein a reference value of the quantitative calcium score is known for the calibration object or is determined, and
    selecting the amount to be set such that an evaluation value of at least one calibration dataset corresponds to the reference value.

6. The method of claim 2, wherein the determining the quantitative calcium score includes,
    selecting an amount of the calcium base vector for setting a calcium contrast based on calibration data.

7. The method of claim 6, wherein the selecting the amount of the calcium base vector includes,
    recording calibration datasets with contrast agent for at least one calibration object, wherein a reference value of the quantitative calcium score is known for the calibration object or is determined, and
    selecting the amount to be set such that an evaluation value of at least one calibration dataset corresponds to the reference value.

8. The method of claim 6, further comprising:
    selecting weightings of the first attenuation value and the second attenuation value are to determine a mixed image attenuation value as a function of the selected amount when a mixed image outside of the permissible attenuation value range is used.

9. The method of claim 2, wherein the determining the quantitative calcium score determines the quantitative calcium score based on a user-side selection of calcifications in a displayed calcium image dataset.

10. The method of claim 1, wherein the determining the quantitative calcium score includes,
    selecting an amount of the calcium base vector for setting a calcium contrast based on calibration data.

11. The method of claim 10, wherein the selecting the amount of the calcium base vector includes,
    recording calibration datasets with contrast agent for at least one calibration object, wherein a reference value of the quantitative calcium score is known for the calibration object or is determined, and
    selecting the amount to be set such that an evaluation value of at least one calibration dataset corresponds to the reference value.

12. The method of claim 10, further comprising:
    selecting weightings of the first attenuation value and the second attenuation value are to determine a mixed image attenuation value as a function of the selected amount when a mixed image outside of a permissible attenuation value range is used.

13. The method of claim 10, wherein at least one of the determining the quantitative calcium score includes determining an Agatston score is determined as the quantitative calcium score, or
    evaluating the dual-energy computed tomography dataset for lesions in a coronary vascular tree, the dual-energy computed tomography dataset being a coronary computed tomography angiography dataset.

14. The method of claim 13, further comprising:
    recording the dual-energy computed tomography dataset using at least one of two different transmit spectra of at least one x-ray source or a photon-counting x-ray detector.

15. The method of claim 1, wherein the determining the quantitative calcium score determines the quantitative calcium score based on a user-side selection of calcifications in a displayed calcium image dataset.

16. The method of claim 1, wherein at least one of
    the determining the quantitative calcium score includes determining an Agatston score is determined as the quantitative calcium score, or
    evaluating the dual-energy computed tomography dataset for lesions in a coronary vascular tree, the dual-energy computed tomography dataset being a coronary computed tomography angiography dataset.

17. The method of claim 1, further comprising:
    recording the dual-energy computed tomography dataset using at least one of two different transmit spectra of at least one x-ray source or a photon-counting x-ray detector.

18. A non-transitory computer readable medium including instructions that, when executed by an evaluation facility, cause the evaluation facility to perform the method of claim 1.

19. A non-transitory electronically readable data carrier including instructions that, when executed by an evaluation facility, cause the evaluation facility to perform the method of claim 1.

20. An evaluation facility comprising:
- a first interface configured to receive an angiographic dual-energy computed tomography dataset recorded using a contrast agent comprising iodine, the angiographic dual-energy computed tomography dataset comprises an image vector for each pixel, the image vector being formed by a first attenuation value assigned to a high-energy spectrum and a second attenuation value assigned to a low-energy spectrum;
- a storage means storing a calcium base vector and an iodine base vector in a two-dimensional dual-energy space spanned by the first attenuation value as an x-axis and the second attenuation value as a y-axis, a base material decomposition being based on the two-dimensional dual-energy space;
- a modification unit configured to determine a modified dual-energy computed tomography dataset by projecting all image vectors in the dual-energy space below a straight line onto the straight line, the straight line defined by the calcium base vector;
- a base material decomposition unit configured to perform the base material decomposition of the modified dual-energy computed tomography dataset to determine a calcium image dataset;
- a determination unit configured to determine a quantitative calcium score from the calcium image dataset; and
- a second interface configured to output the quantitative calcium score.

* * * * *